US008303942B2

(12) United States Patent
Aimi et al.

(10) Patent No.: US 8,303,942 B2
(45) Date of Patent: Nov. 6, 2012

(54) COMPOSITION FOR HAIR

(75) Inventors: Makiko Aimi, Kanagawa (JP); Kazutaka Ogiwara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/014,342

(22) Filed: Jan. 26, 2011

(65) Prior Publication Data

US 2011/0117045 A1 May 19, 2011

Related U.S. Application Data

(63) Continuation of application No. 12/018,973, filed on Jan. 24, 2008, now abandoned.

(30) Foreign Application Priority Data

Jan. 24, 2007 (JP) ................................. 2007/013262
May 17, 2007 (JP) ................................. 2007/131370

(51) Int. Cl.

| | |
|---|---|
| ***A61K 8/64*** | (2006.01) |
| ***A61K 9/14*** | (2006.01) |
| ***A61K 9/51*** | (2006.01) |
| ***A61K 9/38*** | (2006.01) |
| ***A61K 9/64*** | (2006.01) |

(52) U.S. Cl. ..................... 424/70.14; 424/489; 514/775; 514/880; 977/773

(58) Field of Classification Search ........................ None
See application file for complete search history.

(56) References Cited

U.S. PATENT DOCUMENTS

| | | | | |
|---|---|---|---|---|
| 5,053,219 | A * | 10/1991 | Giddey et al. | 424/63 |
| 5,173,322 | A * | 12/1992 | Melachouris et al. | 426/580 |
| 5,405,609 | A * | 4/1995 | Sanchez | 424/744 |
| 5,527,492 | A * | 6/1996 | Hayakawa | 510/131 |
| 2002/0102228 | A1* | 8/2002 | Dunlop et al. | 424/70.1 |
| 2004/0171693 | A1* | 9/2004 | Gan et al. | 514/565 |
| 2004/0213853 | A1 | 10/2004 | Byard et al. | |

FOREIGN PATENT DOCUMENTS

| | | | |
|---|---|---|---|
| JP | 6-503259 | A | 4/1994 |
| JP | 7-504115 | A | 5/1995 |
| JP | 11-221028 | A | 8/1999 |
| JP | 2002-255931 | A | 9/2002 |
| JP | 2002-308728 | A | 10/2002 |
| JP | 2003-526715 | A | 9/2003 |
| JP | 2006-115751 | A | 5/2006 |
| WO | 92-10287 | A1 | 6/1992 |
| WO | 93/08908 | A1 | 5/1993 |
| WO | 01/64046 | A2 | 9/2001 |
| WO | 2007-014755 | A1 | 2/2007 |
| WO | 2007-114262 | A1 | 10/2007 |

OTHER PUBLICATIONS

Aboumahmoud, R. and Savello, P., "Crosslinking of Whey Protein by Transglutaminase." J. Dairy Sci., Vo. 73, pp. 256-263, 1990.
CAS Registry Record 137-66-6, 2 pp., Entered STN Nov. 16, 1984.
Das, Saikat et al, "Aspirin Loaded Albumin Nanoparticles by Coacervation: Implications in Drug Delivery", Trends Biomater. Artif. Organs, vol. 18(2), pp. 203-212, 2005.
Gunasekaran, Sundaram et al, "Use of whey proteins for encapsulation and controlled delivery applications", Journal of Food Engineering, vol. 83, pp. 31-40, 2007.
Hall, Alastair, "The Vitamin for Hair Loss", the Alternative Health Daily. Originally published Jun. 23, 2006.
Semo, Efrat et al, "Casein micelle as a natural nano-capsular vehicle for nutraceuticals", Food Hydrocolloids, vol. 21, pp. 936-942, 2007.
Thies, Curt, "Microencapsulation", Kirk-Othmer Encyclopedia of Chemical Technology, John Wiley & Sons, 2005.
Japanese Office Action dated Dec. 20, 2011, corresponding to JP Application No. 2007-131370.

* cited by examiner

*Primary Examiner* — Frederick Krass
*Assistant Examiner* — Isaac Shomer
(74) *Attorney, Agent, or Firm* — Sughrue Mion, PLLC

(57) ABSTRACT

It is an object of the present invention to provide a composition for hair which comprises highly safe nanoparticles having high transparency due to the small particle size and high permeability into hair and scalp. The present invention provides a composition for hair which comprises protein nanoparticles containing an active ingredient for hair.

2 Claims, 4 Drawing Sheets a b a b a b a b a b a b a b a b

COMPOSITION FOR HAIR

This is a continuation of U.S. patent application Ser. No. 12/018,973, filed Jan. 24, 2008, which claims priority from Japan Patent Application Nos. 013262/2007 filed Jan. 24, 2007 and 131370/2007 filed May 17, 2007. The entire disclosures of each of the prior applications are considered part of this continuation application and are incorporated herein by reference.

TECHNICAL FIELD

The present invention relates to a composition for hair, which comprises protein nanoparticles containing an active ingredient for hair.

BACKGROUND ART

Extensive applications of fine particle ~materials have been expected for biotechnology. In particular, the application of nanoparticle materials generated based on the advancement of nanotechnology to food, cosmetics, pharmaceutical products, and the like has been actively discussed. In this regard, the results of many studies have been reported.

For instance, regarding cosmetics, more obvious skin-improving effects have been required in recent years. Manufactures have been attempting to improve the functionality and usability of their own products and to differentiate their own products from competitive products by applying a variety of technologies such as nanotechnology. In general, the stratum corneum serves as a barrier for the skin. Thus, medicines are unlikely to permeate therethrough into the skin. In order to obtain sufficient skin-improving effects, it is essential to improve the skin permeability of active ingredients. In addition, it is difficult to formulate many active ingredients due to poor preservation stability or tendency to result in skin irritancy, although they are highly effective to the skin. In order to solve the above problems, a variety of fine particle materials have been under development for the improvement of transdermal absorption and preservation stability, reduction of skin irritancy, and the like. Recently, a variety of fine particle materials such as ultrafine emulsions and liposomes have been studied (e.g., Mitsuhiro Nishida, Fragrance Journal, Nov., 17 (2005)).

With the use of polymeric materials instead of emulsified products or liposomes, it can be expected that remarkable improvement in preservation stability and in in vivo particle stability will be achieved due to the structure of such material. However, in most studies, synthetic polymers obtained by, for example, emulsion polymerization are used, so that it is required to obtain safer carriers.

Further, Hiroki Fukui, Polymer, October, 798 (2006) describes the study of reservoir properties of a phospholipid polymer nanoparticle whereby an active ingredient is maintained in hair. However, it is not easy to design and synthesize such self-organized polymer. Thus, it is difficult to commercialize such polymer in terms of cost.

As an aside, hair is damaged by environmental factors such as ultraviolet irradiation and chlorine contact, chemical factors such as coloring, decoloring, permanent wave, and hair washing with the use of shampoos comprising strong surfactants, and physical factors such as the overuse of dryers at high temperatures.

Such damage results in unfavorable hair conditions such as loss of cuticles or proteins and hardened, brittle, or split hair.

Hitherto, many ingredients have been said to be effective for treatment or prevention of hair damage. Such ingredients have been used for protection of hair from ultraviolet rays or dryness, enhancement of hair volume or strength, prevention of hair loss, improvement against hair decrease, and the like. However, the above ingredients are not sufficiently effective.

Meanwhile, it is also important for a hair growth agent not only to contain an excellent hair growth component but also to have an active ingredient that can be securely delivered to action sites.

In addition, some compositions for hair contain 50% or more ethanol, and its adverse effects on the scalp are causes for concern. In the field of hair growth agents, hair growth agents generally contain 50% or more ethanol in order to dissolve hydrophobic hair growth components so that adverse effects caused by ethanol are causes for concern. JP Patent Publication (Kokai) No. 2006-176447 A suggests that scalp irritation caused by ethanol can be alleviated by a composition for hair.

DISCLOSURE OF THE INVENTION

It is an object of the present invention to solve the above problems of the prior art. Specifically, it is an object of the present invention to provide a composition for hair which comprises highly safe nanoparticles having high transparency due to the small particle size and high permeability into hair and scalp, such composition being formulated as a shampoo, a rinse, a hair conditioner, a hair pack, a hair liquid, a hair tonic, a hair spray, or the like.

As a result of intensive studies in order to achieve the above object, the present inventors demonstrated that protein nanoparticles containing an active ingredient for hair which were prepared by the inventors are highly safe and have high transparency and favorable permeability into hair and scalp. The present invention has been completed based on the above findings.

That is, the present invention provides a composition for hair which comprises protein nanoparticles containing an active ingredient for hair.

Preferably, the composition comprises 0.01% to 50% by weight protein nanoparticles.

Preferably, the average particle size of protein nanoparticles is 10 to 1000 nm.

Preferably, the protein nanoparticles contain an active ingredient for hair in a weight that is 0.1% to 100% of the protein weight.

Preferably, the active ingredient for hair is at least one selected from the group consisting of cosmetic ingredients and pharmaceutical ingredients.

More preferably, the active ingredient for hair is an ionic substance or a fat-soluble substance.

Further preferably, the active ingredient for hair is a hair growth agent.

Preferably, the ethanol content in the composition for hair of the present invention is 20% by weight or less.

Preferably, the protein is at least one selected from the group consisting of collagen, gelatin, acid-treated gelatin, albumin, ovalbumin, casein, transferrin, globulin, fibroin, fibrin, laminin, fibronectin, and vitronectin.

Preferably, the protein is subjected to crosslinking treatment during and/or after nanoparticle formation.

Preferably, an enzyme can be used as a crosslinking agent.

The enzyme is not particularly limited as long as it has the effect of causing protein crosslinking. However, transglutaminase can be preferably used.

Preferably, the composition for hair of the present invention comprises casein nanoparticles prepared by the following steps (a) to (c):

(a) mixing casein with a basic aqueous medium at pH of from 8 to less than 11;
(b) adding at least one active ingredient for hair to the solution obtained in step (a); and
(c) injecting the solution obtained in step (b) into an acidic aqueous medium at pH of 3.5 to 7.5:

Preferably, the composition for hair of the present invention comprises casein nanoparticles prepared by the following steps (a) to (c):

(a) mixing casein with a basic aqueous medium at pH of from 8 to less than 11;
(b) adding at least one active ingredient for hair to the solution obtained in step (a); and
(c) lowering the pH of the solution obtained in step (b) to pH value which is different from the isoelectric point by 1 or more units, while stirring the solution.

The particles containing an active ingredient for hair in the composition for hair of the present invention are nanoparticles, and thus they are highly absorbable. In addition, according to the present invention: since protein nanoparticles are used, there is no need to use chemical crosslinking agents or synthetic surfactants for production of the composition, which is highly safe. Moreover, a hydrophobic active ingredient for hair can be formed in a nanoparticle dispersion. Accordingly, there is no need to add ethanol in large amounts and thus scalp irritancy caused by ethanol can be substantially prevented.

BEST MODE FOR CARRYING OUT THE INVENTION

Figure 1:
FIG. 1 shows the results of fluorescence microscopic observation in Comparative example 2.
Figure 2:
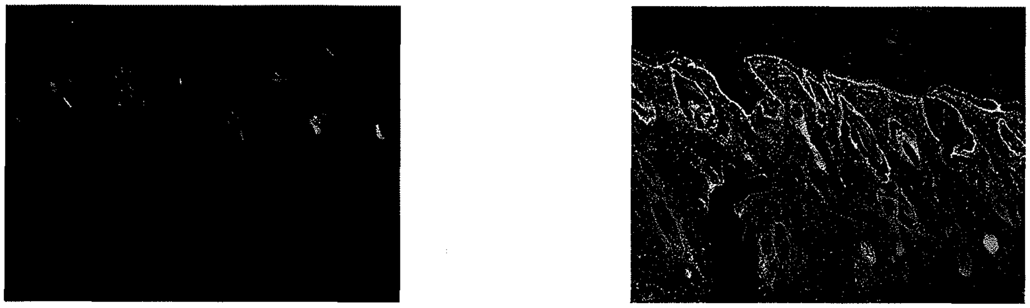
FIG. 2 shows the results of fluorescence microscopic observation in Comparative example 3.
Figure 3:
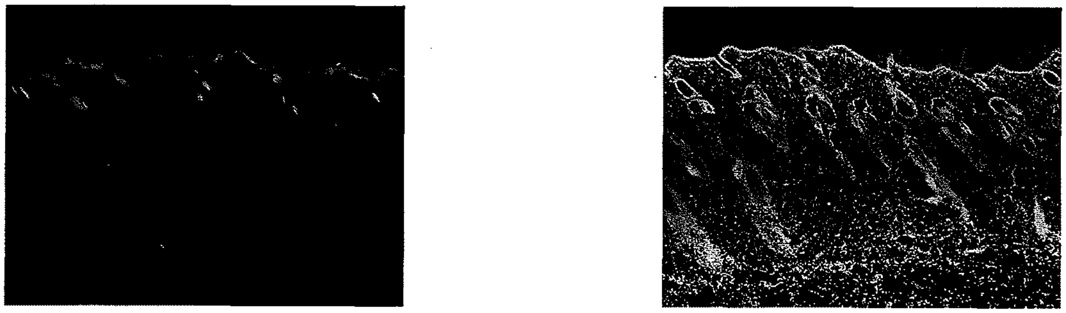
FIG. 3 shows the results of fluorescence microscopic observation in Comparative example 4.
Figure 4:
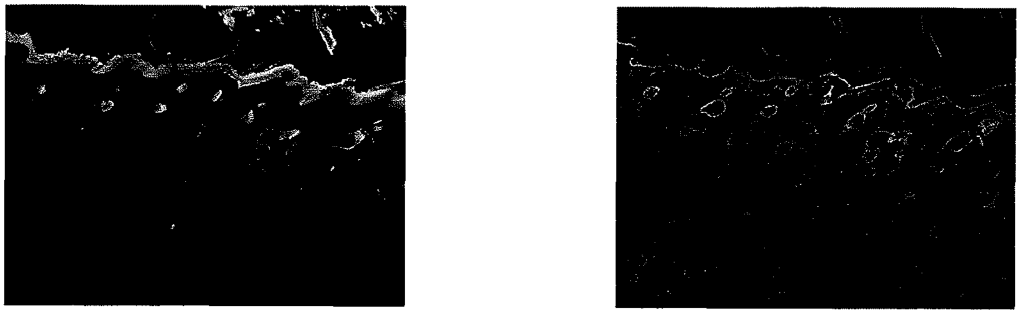
FIG. 4 shows the results of fluorescence microscopic observation in Test example 2.
Figure 5:
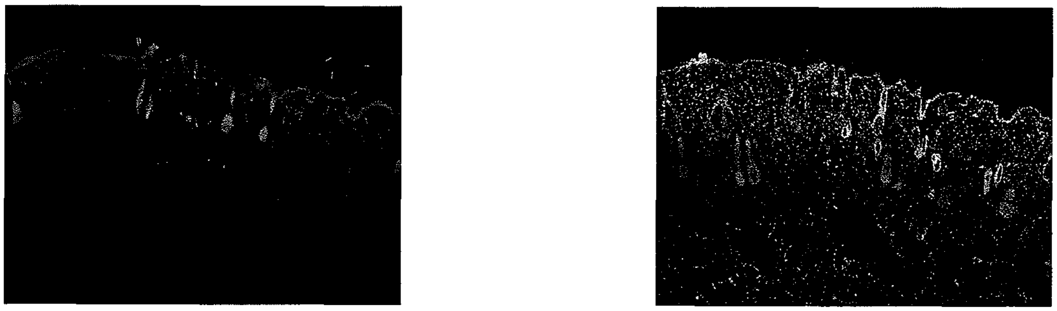
FIG. 5 shows the results of fluorescence microscopic observation in Comparative example 5.
Figure 6:
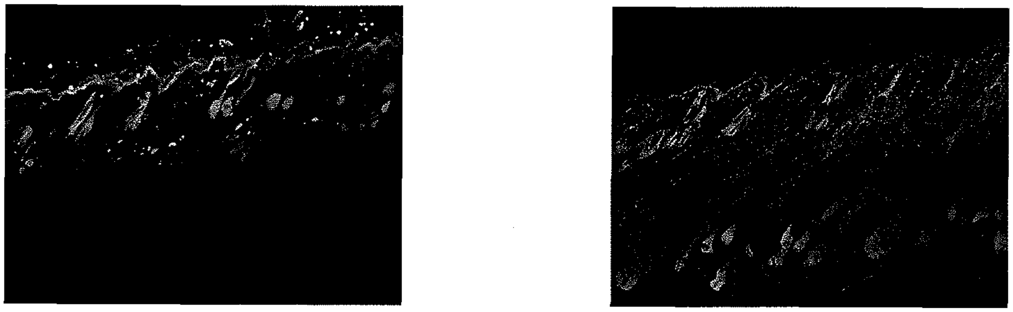
FIG. 6 shows the results of fluorescence microscopic observation in Test example 3.

Hereafter, embodiments of the present invention will be specifically described.

The composition for hair of the present invention is characterized in that it comprises protein nanoparticles containing an active ingredient for hair.

The type of active ingredient for hair used in the present invention is not particularly limited. However, the active ingredient can be selected from among cosmetic ingredients, quasi-drug ingredients, pharmaceutical ingredients, and the like. According to the present invention, specific examples of an active ingredient for hair contained in protein nanoparticles that can be selected may include moisturizing agents, ultraviolet absorbing agents, free-radical-removing agents, antioxidants, anti-inflammatory agents, blood circulation promoters, hair growth agents, hair nutritional supplements, anti-aging agents, collagen synthesis promoters, vitamins, minerals, and amino acids.

Examples of moisturizing agents include agar, diglycerin, distearyldimonium hectorite, butylene glycol, polyethylene glycol, propylene glycol, hexylene glycol, *Coix lachrma-jobi* extract, vaseline, urea, hyaluronic acid, ceramide, Lipidure, isoflavone, amino acid, collagen, mucopolysaccharide, fucoidan, lactoferrin, sorbitol, chitin/chitosan, malic acid, glucuronic acid, placenta extract, seaweed extract, moutan cortex extract, sweet tea extract, hypericum extract, coleus extract, *Euonymus japonicus* extract, safflower extract, *Rosa rugosa* flower extract, *Polyporus sclerotium* extract, hawthorn extract, rosemary extract, duke extract, chamomile extract, *Lamium album* extract, *Litchi Chinensis* extract, *Achillea millefolium* extract, aloe extract, marronnier extract, *Thujopsis dolabrata* extract, Fucus extract, Osmoin extract, oat bran extract, tuberosa polysaccharide, *Cordyceps sinensis* (plant worm) extract, barley extract, orange extract, *Rehmannia glutinosa* extract, zanthoxylumb extract, and *Coix lachrma-jobi* extract. In addition, in the cases of casein nanoparticles, casein itself has moisture retention capacity.

Examples of ultraviolet protecting agents include homomethyl salicylate, 4-methoxycinnamic acid-2-ethylhexyl, 2-hydroxy-4-methoxy benzophenone, 2-hydroxy-4-methoxy benzophenone sulfonic acid, 2-hydroxy-4-methoxy benzophenone sodium sulfonate, 4-t-butyl-4'-methoxy-dibenzoylmethane, titanium oxide, and zinc oxide.

Examples of free-radical-removing agents include superoxide dismutase (SOD), mannitol, carotenoids such as beta carotene, astaxanthin, rutin and derivatives thereof, bilirubin, cholesterol, tryptophan, histidine, quercetin, quercitrin, catechin, catechin derivatives, gallic acid, gallic acid derivatives, *Scutellariae radix* extract, ginkgo extract, *Saxifraga stolonifera* (strawberry geranium) extract, melissa extract, *Geranium thunbergii* extract, moutan cortex extract, parsley extract, tormentilla extract, *Momordica grosvenori* extract, seaweed extract, "Yashajitsu" (*Alnus firma* Sieb. et Zucc.) extract, and Lycii cortex extract.

Examples of antioxidants include carotenes, retinoic acid, retinol, vitamin C and derivatives thereof, kinetin, astaxanthin, tretinoin, vitamin E and derivatives thereof, sesamin, α-lipoic acid, coenzyme Q10, flavonoids, erythorbic acid, gallic acid propyl, BHT (di-n-butylhydroxytoluene), BHA (butylhydroxyanisole), *Engelhardtia chrysolepis* Hance extract, soybean extract, black tea extract, green tea extract, and *Rosae multiflorae fructus* extract.

Examples of anti-inflammatory agents include: compounds and salts and derivatives thereof selected from the group consisting of azulene, guaiazulene, diphenhydramine hydrochloride, hydrocortisone acetate, predonisolone, glycyrrhizic acid, glycyrrhetic acid, mefenamic acid, phenylbutazone, indomethacin, ibuprofen, and ketoprofen; and plant extracts selected from the group consisting of *Scutellariae radix* extract, *Artemisia capillaris* extract, balloonflower (*Platycodon grandiflorus*) extract, *Armeniacae semen* extract, gardenia extract, *Sasa veitchii* extract, gentiana extract, comfrey extract, white birch extract, mallow extract, *Persicae semen* extract, peach leaf extract, and *Eriobotryae folium* extract.

Examples of blood circulation promoters that can be selected include nicotinic acid, *Swertia japonica* extract, γ-oxazole, alkoxycarbonylpyridine N-oxide, carpronium chloride, and acetylcholine or derivatives thereof.

Examples of hair growth agents include glycyrrhetic acid or derivatives thereof, glycyrrhizic acid or derivatives thereof, hinokitiol, minoxidil and analogs thereof, adenosine, vitamin E and derivatives thereof, vitamin C derivatives, 6-benzyl aminopurine, nicotinic acid benzyl, nicotinic acid tocopherol, nicotinic acid β-butoxy ester, isopropyl methylphenol, pentadecanoic acid and derivatives thereof, cephalathin, finasteride, t-flavanone, and pantothenyl ethyl ether. Among them, hinokitiol and minoxidil or analogs thereof are most preferable.

Also, known ingredients can be used as anti-aging agents, collagen synthesis promoters, vitamins, minerals, and amino acids.

The above active ingredients for hair may be used alone or in combinations of two or more.

According to the present invention, it was found that, with the use of interaction between a fat-soluble active ingredient for hair and a casein hydrophobic domain, it is possible for casein nanoparticles to contain the active ingredient for hair. Further, it was found that such particles remain stable in an aqueous solution. The ClogP of a fat-soluble substance is preferably more than 0 and more preferably not less than 1.

Further, it was found that a particle mixture of protein and ionic polysaccharide or another ionic protein can contain an ionic active ingredient for hair.

The composition for hair of the present invention comprises preferably 0.01% to 50% by weight and most preferably 0.1% to 10% by weight protein nanoparticles.

The composition for hair of the present invention contains an active ingredient for hair in a weight that is preferably 0.1% to 100% and more preferably 0.1% to 50% of the protein weight.

According to the present invention, an active ingredient for hair may be added during or after protein nanoparticle formation.

Further, the composition for hair of the present invention may comprise, as an additive, an active ingredient for hair. Specific examples of active ingredients for hair that serve as additives include, but are not limited to, pantothenic acid, panthenol, licorice extract, *Lepisorus thunbergianus* extract, *Sophorae Radix* (sophora root) extract, *Swertia japonica extract, capsicum* extract, *Ampelopsis cantoniensis* var. *grossedentata* extract, carrot extract, *Taraxacum mongolicum* Hand.-Mazz. extract, tree peony extract, and mandarin orange extract.

The average particle size of protein nanoparticles used in the present invention is generally 1 to 1000 nm, preferably 10 to 1000 nm, more preferably 10 to 200 nm, further preferably 10 to 100 nm, and particularly preferably 20 to 50 nm.

The type of protein used in the present invention is not particularly limited. However, a protein having a lysine residue and a glutamine residue is preferable. In addition, such protein having a molecular weight of approximately 10,000 to 1,000,000 is preferably used. The origin of the protein is not particularly limited. However, a human-derived protein is preferably used. Specific examples of a protein that can be used include, but are not limited to, the following compounds according to the present invention: at least one selected from the group consisting of collagen, gelatin, acid-treated gelatin, albumin, ovalbumin, casein, transferrin, globulin, fibroin, fibrin, laminin, fibronectin, and vitronectin. In addition, the origin of the protein is not particularly limited. Thus, any bovine, swine, or fish protein, as well as recombinant protein of any thereof, can be used. Examples of recombinant gelatin that can be used include, but are not limited to, gelatins described in EP1014176 A 2 and U.S. Pat. No. 6,992,172. Among them, casein, acid-treated gelatin, collagen, or albumin is preferable. Further, casein or acid-treated gelatin is most preferable.

Upon the use of casein according to the present invention, the origin of the casein is not particularly limited. Casein may be milk-derived or bean-derived. Any of α-casein, β-casein, γ-casein, and κ-casein, as well as a mixture of any thereof, can be used. Also, a recombinant thereof can be used. Preferably, casein sodium can be used. Caseins may be used alone or in combinations of two or more.

Proteins used in the present invention may be used alone or in combinations of two or more.

According to the present invention, it is possible to carry out a crosslinking treatment for a protein during and/or after nanoparticle formation. For the crosslinking treatment, an enzyme can be used. Any enzyme may be used without particular limitation as long as it has been known to have the effect of causing protein crosslinking. Among such enzymes, transglutaminase is preferable.

Transglutaminase may be derived from a mammal or a microorganism. A recombinant transglutaminase can be used. Specific examples thereof include the Activa series by Ajinomoto Co., Inc., commercially available mammalian-derived transglutaminase serving as a reagent, such as guinea pig liver-derived transglutaminase, goat-derived transglutaminase, rabbit-derived transglutaminase, or human-derived recombinant transglutaminase produced by, for example, Oriental Yeast Co., Ltd., Upstate USA Inc., and Biodesign International.

The amount of an enzyme used in a crosslinking treatment according the present invention can be adequately determined depending upon protein type. In general, an enzyme can be added in a weight that is 0.1% to 100% and preferably approximately 1% to 50% of the protein weight.

The duration for an enzymatic crosslinking reaction can be adequately determined depending upon protein type and nanoparticle size. However, in general, the reaction can be carried out for 1 to 72 and preferably 2 to 24 hours.

The temperature for an enzymatic crosslinking reaction can be adequately determined depending upon protein type and nanoparticle size. In general, the reaction can be carried out at 0° C. to 80° C. and preferably at 25° C. to 60° C.

Enzymes used in the present invention may be used alone or in combinations of two or more.

Nanoparticles of the present invention can be prepared in accordance with Patent Document: JP Patent Publication (Kokai) No. 6-79168 A (1994); or C. Coester, Journal Microcapsulation, 2000, vol. 17, pp. 187-193, provided that an enzyme is preferably used instead of glutaraldehyde for a crosslinking method.

In addition, according to the present invention, the enzymatic crosslinking treatment is preferably carried out in an organic solvent. The organic solvent used herein is preferably an aqueous organic solvent such as ethanol, isopropanol, acetone, or THF.

Further, according to the present invention, it is preferable to remove an organic solvent by distillation subsequent to a crosslinking treatment, followed by water dispersion. It is also possible to add water prior to or subsequent to removal of an organic solvent by distillation.

It is also possible to add at least one component selected from the group consisting of lipids (e.g., phospholipid), anionic polysaccharides, cationic polysaccharides, anionic proteins, cationic proteins, and cyclodextrin to the composition for hair of the present invention. The amounts of lipid (e.g. phospholipid), anionic polysaccharide, cationic polysaccharide, anionic protein, cationic protein, and cyclodextrin to be added are not particularly limited. However, they can be added usually in a weight that is 0.1% to 100% of the protein weight. In the case of the composition for hair of the present invention, it is possible to adjust the release rate by changing the ratio of the above components to the protein.

Specific examples of phospholipids that can be used in the present invention include, but are not limited to, the following compounds according to the present invention: phosphatidylcholine (lecithin), phosphatidylethanolamine, phosphatidylserine, phosphatidylinositol, phosphatidylglycerol, diphosphatidylglycerol, and sphingomyelin.

Anionic polysaccharides that can be used in the present invention are polysaccharides having an acidic polar group such as a carboxyl group, a sulfate group, or a phosphate group. Specific examples thereof include, but are not limited to, the following compounds according to the present invention: chondroitin sulfate, dextran sulfate, carboxymethyl cellulose, carboxymethyl dextran, alginic acid, pectin, carrageenan, fucoidan, agaropectin, porphyran, karaya gum, gellan gum, xanthan gum, and hyaluronic acids.

Cationic polysaccharides that can be used in the present invention are polysaccharides having a basic polar group such as an amino group. Examples thereof include, but are not limited to, the following compounds according to the present invention: polysaccharides such as chitin or chitosan, which comprise, as a monosaccharide unit, glucosamine or galactosamine.

Anionic proteins that can be used in the present invention are proteins and lipoproteins having a more basic isoelectric point than the physiological pH. Specific examples thereof include, but are not limited to, the following compounds according to the present invention: poly glutamic acid, polyaspartic acid, lysozyme, cytochrome C, ribonuclease, trypsinogen, chymotrypsinogen, and α-chymotrypsin.

Cationic proteins that can be used in the present invention are proteins and lipoproteins having a more acidic isoelectric point than the physiological pH. Specific examples of such cationic protein include, but are not limited to, the following compounds according to the present invention: polylysine, polyarginine, histone, protamine, and ovalbumin.

According to the present invention, it is possible to use casein nanoparticles prepared by the following steps ((a) to (c)) of:

(a) mixing casein with a basic aqueous medium at pH of 8 to less than 11;

(b) adding at least one active ingredient for hair to the solution obtained in step (a); and (c) injecting the solution obtained in step (b) into an acidic aqueous medium at pH of 3.5 to 7.5.

Further, according to the present invention, it is possible to use casein nanoparticles prepared by the following steps ((a) to (c)) of:

(a) mixing casein with a basic aqueous medium at pH of from 8 to less than 11;

(b) adding at least one active ingredient for hair to the solution obtained in step (a); and (c) lowering the pH of the solution obtained in step (b) to pH value which is different from the isoelectric point by 1 or more units, while stirring the solution.

According to the present invention, it is possible to prepare casein nanoparticles of desired sizes. Also, with the use of interaction between a hydrophobic active ingredient for hair and a casein hydrophobic domain, it is possible for casein nanoparticles to contain the active ingredient for hair. In addition, it was found that such particles remain stable in an aqueous solution.

Further, it was found that a particle mixture of casein and ionic polysaccharide or another ionic protein can contain an ionic active ingredient for hair.

The method for preparing casein nanoparticles of the present invention involves a method wherein casein is mixed with a basic aqueous medium solution and the solution is injected into an acidic aqueous medium, and a method wherein casein is mixed with a basic aqueous medium and the pH of the medium is lowered during stirring, for example.

The method wherein casein is mixed with a basic aqueous medium solution and the solution is injected into an acidic aqueous medium is preferably carried out using a syringe for convenience. However, there is no particular limitation as long as the injection rate, solubility, temperature, and stirring conditions are satisfied. Injection can be carried out usually at an injection rate of 1 mL/min to 100 mL/min. The temperature of the basic aqueous medium can be adequately determined. In general, the temperature is 0° C. to 80° C. and preferably 25° C. to 70° C. The temperature of an aqueous medium can be adequately determined. In general, the temperature can be 0° C. to 80° C. and preferably 25° C. to 60° C. The stirring rate can be adequately determined. However, in general, the stirring rate can be 100 rpm to 3000 rpm and preferably 200 rpm to 2000 rpm.

In the method wherein casein is mixed with a basic aqueous medium and the pH of the medium is lowered during stirring, it is preferable to add acid dropwise for convenience. However, there is no particular limitation as long as solubility, temperature, and stirring conditions are satisfied. The temperature of a basic aqueous medium can be adequately determined. However, in general, the temperature can be 0° C. to 80° C. and preferably 25° C. to 70° C. The stirring rate can be adequately determined. However, in general, the stirring rate can be 100 rpm to 3000 rpm and preferably 200 rpm to 2000 rpm.

The aqueous medium that can be used for the present invention is an aqueous solution or a buffer comprising an organic acid or base or an inorganic acid or base.

Specific examples thereof include, but are not limited to, aqueous solutions comprising: organic acids such as citric acid, ascorbic acid, gluconic acid, carboxylic acid, tartaric acid, succinic acid, acetic acid, phthalic acid, trifluoroacetic acid, morpholinoethanesulfonic acid, and 2-[4-(2-hydroxyethyl)-1-piperazinyl]ethanesulfonic acid; organic bases such as tris (hydroxymethyl), aminomethane, and ammonia; inorganic acids such as hydrochloric acid, perchloric acid, and carbonic acid; and inorganic bases such as sodium phosphate, potassium phosphate, calcium hydroxide, sodium hydroxide, potassium hydroxide, and magnesium hydroxide.

The concentration of an aqueous medium used in the present invention is preferably approximately 10 mM to 1 M, and more preferably approximately 20 mM to 200 mM.

The pH of a basic aqueous medium used in the present invention is preferably 8 or more, more preferably 8 to 12, and further preferably 10 to 12. When the pH is excessively high, there is concern regarding hydrolysis or risks in handling. Thus, the pH is preferably in the above range.

According to the present invention, the temperature at which casein is mixed with a basic aqueous medium at a pH of 8 or more is preferably 0° C. to 90° C., more preferably 10° C. to 80° C., and further preferably 20° C. to 70° C.

The pH of an acidic aqueous medium used in the present invention is preferably 3:5 to 7.5 and more preferably 5 to 6. When the pH does not fall in the above range, the particle size tends to become large.

The composition for hair of the present invention may further comprise an additive. Examples of an additive that can be used include, but are not limited to, at least one selected from the group consisting of softening agents, transdermal absorption enhancers, soothing agents, preservatives, antioxidants, coloring agents, thickeners, aroma chemicals, and pH adjusters.

Specific examples of softening agents that can be used in the present invention include, but are not limited to, the following compounds according to the present invention: glycerin, mineral oil, and emollient ingredients (e.g., isopropyl isostearate, polyglyceryl isostearate, isotridecyl isononanoate, octyl isononanoate, oleic acid, glyceryl oleate, cocoa butter, cholesterol, mixed fatty acid triglyceride, dioctyl succinate, sucrose tetrastearate triacetate, cyclopentasiloxane, sucrose distearate, palmitateoctyl, octyl hydroxystearate, arachidyl behenate, sucrose polybehenate, polymethylsilsesquioxane, myristyl alcohol, cetyl myristate, myristyl myristate, and hexyl laurate).

Specific examples of transdermal absorption enhancers that can be used in the present invention include, but are not limited to, the following compounds according to the present invention: ethanol, isopropyl myristate, citric acid, squalane, oleic acid, menthol, N-methyl-2-pyrrolidone, diethyl adipate, diisopropyl adipate, diethyl sebacate, diisopropyl sebacate, isopropyl palmitate, oleic acid isopropyl, oleic acid octyldodecyl, isostearyl alcohol, 2-octyldodecanol, urea, vegetable oil, and animal oil.

Specific examples of soothing agents that can be used in the present invention include, but are not limited to, the following compounds according to the present invention: benzyl alcohol, procaine hydrochloride, xylocalne hydrochloride, and chlorobutanol.

Specific examples of preservatives that can be used in the present invention include, but are not limited to, the following compounds according to the present invention: benzoic acid, sodium benzoate, paraben, ethylparaben, methylparaben, propylparaben, butylparaben, potassium sorbate, sodium sorbate, sorbic acid, sodium dehydroacetate, hydrogen peroxide, formic acid, ethyl formate, sodium hypochlorite, propionic acid, sodium propionate, calcium propionate, pectin degradation products, polylysine, phenol, isopropylmethyl phenol, orthophenylphenol, phenoxyethanol, resorcin, dibutylhydroxytoluene. (BHT), thymol, thiram, tea tree oil, hinokitiol, glycerin, dipropylene glycol, 1.3-butylene glycol, 1.4-butylene glycol, 1,2-pentanediol, and 2-methyl-2,4-pentanediol.

Specific examples of antioxidants that can be used in the present invention include, but are not limited to, the following compounds according to the present invention: vitamin A, retinoic acid, retinol, retinol acetate, retinol palmitate, retinyl acetate, retinyl palmitate, tocopheryl retinoate, vitamin C and derivatives thereof, kinetin, β-carotene, astaxanthin, lutein, lycopene, tretinoin, vitamin E, α-lipoic acid, coenzyme Q10, polyphenol, SOD, and phytic acid.

Specific examples of coloring agents that can be used in the present invention include, but are not limited to, the following compounds according to the present invention: krill pigment, orange dye, cacao dye, kaoline, carmines, ultramarine blue, cochineal dye, chrome oxide, iron oxide, titanium dioxide, tar dye, and chlorophyll.

Specific examples of thickeners that can be used in the present invention include, but are not limited to, the following compounds according to the present invention: quince seed, carrageenan, gum arabic, karaya gum, xanthan gum, gellan gum, tamarind gum, locust bean gum, gum traganth, pectin, starch, cyclodextrin, methylcellulose, ethylcellulose, carboxymethylcellulose, sodium alginate, polyvinyl alcohol, polyvinyl pyrrolidone, carboxyvinyl polymer, and sodium polyacrylate.

Specific examples of aroma chemicals that can be used in the present invention include, but are not limited to, the following compounds according to the present invention: musk, acacia oil, anise oil, ylang ylang oil, cinnamon oil, jasmine oil, sweet orange oil, spearmint oil, geranium oil, thyme oil, neroli oil, mentha oil, hinoki (Japanese cypress) oil, fennel oil, peppermint oil, bergamot oil, lime oil, lavender oil, lemon oil, lemongrass oil, rose oil, rosewood oil, anisaldehyde, geraniol, citral, civetone, muscone, limonene, and vanillin.

Specific examples of pH adjusters that can be used in the present invention include, but are not limited to, the following compounds according to the present invention: sodium citrate, sodium acetate, sodium hydroxide, potassium hydroxide, phosphoric acid, and succinic acid.

Examples of the dosage form of the composition for hair of the present invention include, but are not limited to, liquid formulations for external use, fomentations, embrocations, bathing agents, bath additives, disinfectants, ointments, gels, creams, pastes, adhesive skin patches, plasters, wound-surface-covering agents, wound-surface-covering gauzes, hemostatics, adhesives, adhesive tape, adhesive tape for transdermal absorption, wound protective agents, aerosols, lotions, tonics, liniments, emulsions, suspensions, saturants, tinctures, powders, foaming agents, skin lotions, massage creams, nourishing creams, face packs, sheet-type drugs for external use, cosmetics for makeup, skin coloring agents for external use, cosmetic skin adhesives, shampoos, rinses, hair conditioners, hair packs, hair liquids, hair tonics, hair sprays, permanent wave compositions, hair dyes, body soap, soap, bath agents, sun care products (e.g., sunscreens, sun tanning oils, and after-sun lotions), and fragrances.

The composition for hair of the present invention can be administered without particular limitation. For instance, it can be administered by directly applying it to the scalp.

The dose of the composition for hair of the present invention can be adequately determined depending upon type and amount of active ingredient for hair and upon user weight and condition, for example. The dose for single administration is generally approximately 1 μg to 50 $mg/cm^2$ and preferably 2.5 μg to 10 $mg/cm^2$.

The ethanol content in the composition for hair of the present invention is preferably 20% by weight or less, more preferably 10% by weight or less, and most preferably substantially 0% by weight.

The present invention is hereafter described in greater detail with reference to the following examples, although the technical scope of the present invention is not limited thereto.

EXAMPLES

Example 1

Milk-derived casein (100 mg; Wako Pure Chemical Industries, Ltd.) was mixed with 50 mM phosphate buffer (pH 10, 10 mL). Coumarin 6 (0.015 mg: Wako Pure Chemical Industries, Ltd.) was dissolved in ethanol (0.1 mL). The two different solutions were mixed together. Hydrochloric acid was added thereto so that the pH was adjusted to 7.5. Thus, casein nanoparticles were obtained.

The average particle size of the above particles was measured with a "Nanotrac" light scattering photometer (NIKKISO Co., Ltd.) and found to be 29 mu.

Example 2

Milk-derived casein Na (10 mg; Wako Pure Chemical Industries, Ltd.) was mixed with 50 mM phosphate buffer (pH 9, 1 mL). Glycyrrhetic acid (1.7 mg; Wako Pure Chemical Industries, Ltd.) was dissolved in ethanol (0.25 mL). The glycyrrhetic acid solution was added dropwise to the casein solution during stirring. The resulting liquid mixture (1 ml) was injected into 200 mM phosphate buffer water (pH 5, 10 mL) with the use of a microsyringe at an external temperature of 40° C. during stirring at 800 rpm. Thus, a water dispersion of casein nanoparticles containing glycyrrhetic acid was obtained. The average particle size of the above particles was measured with a "Microtrac" light scattering photometer (NIKKISO Co., Ltd.) and found to be 83 nm.

Example 3

Milk-derived casein Na (10 mg; Wako Pure Chemical Industries, Ltd.) was mixed with 50 mM phosphate buffer (pH 9, 1 mL). Hinokitiol (1.7 mg; Wako Pure Chemical Industries, Ltd.) was dissolved in ethanol (0.25 mL). The hinokitiol solution was added dropwise to the casein solution during stirring. The resulting liquid mixture (1 ml) was injected into 200 mM phosphate buffer water (pH 5, 10 mL) with the use of a microsyringe at an external temperature of 40° C. during stirring at 800 rpm. Thus, a water dispersion of casein nanoparticles containing hinokitiol was obtained. The average particle size of the above particles was measured with a "Microtrac" light scattering photometer (NIKKISO Co., Ltd.) and found to be 57 nm.

Example 4

Milk-derived casein Na (10 mg; Wako Pure Chemical Industries, Ltd.) was mixed with 50 mM phosphate buffer (pH 9, 1 mL). Tocopherol acetate (1.7 mg) was dissolved in ethanol (0.25 mL). The tocopherol acetate solution was added dropwise to the casein solution during stirring. The resulting liquid mixture (1 ml: casein solution) was injected into 200 mM phosphate buffer water (10 mL) with the use of a microsyringe at an external temperature of 40° C. during stirring at 800 rpm. Thus, a water dispersion of casein nanoparticles containing tocopherol acetate was obtained. The average particle size of the above particles was measured with a "Microtrac" light scattering photometer (NIKKISO Co., Ltd.) and found to be 124 nm.

Example 5

Milk-derived casein Na (10 mg; Wako Pure Chemical Industries, Ltd.) was mixed with 50 mM phosphate buffer (pH 9, 1 mL). The casein solution (1 ml) was injected into 200 mM phosphate buffer water (pH 5, 10 mL) in which minoxidil (1.7 mg) had been dissolved with the use of a microsyringe at an external temperature of 40° C. during stirring at 800 rpm. Thus, a water dispersion of casein nanoparticles containing minoxidil was obtained. The average particle size of the above particles was measured with a "Microtrac" light scattering photometer (NIKKISO Co., Ltd.) and found to be 55 nm.

Example 6

Acid-treated gelatin (10 mg) and TG-S (5 mg; Ajinomoto Co., Inc.) were dissolved in water (1 mL). The gelatin solution (1 ml) was injected into ethanol (10 mL) in which glycyrrhetic acid (1.7 mg) had been dissolved with the use of a microsyringe at an external temperature of 40° C. during stirring at 800 rpm. Thus, gelatin nanoparticles were obtained. The gelatin nanoparticles were allowed to stand at an external temperature of 55° C. for 5 hours for enzymatic crosslinking. The average particle size of the above particles was measured with a "Microtrac" light scattering photometer (NIKKISO Co., Ltd.) and found to be 80 nm.

Water (5 mL) was added to the obtained gelatin nanoparticle dispersion and ethanol was removed therefrom by means of a rotary evaporator. Thus, a water dispersion of gelatin nanoparticles containing glycyrrhetic acid was obtained. The average particle size of the above particles was measured with a "Microtrac" light scattering photometer (NIKKISO Co., Ltd.) and found to be 201 mu.

Example 7

Milk-derived casein (100 mg; Wako Pure Chemical Industries, Ltd.) was mixed with 50 mM phosphate buffer (pH 10, 10 mL). Hyaluronic acid (1 mg; Wako Pure Chemical Industries, Ltd.) was dissolve in the solution. Hydrochloric acid was added thereto so that the pH was adjusted to 7. Thus, casein nanoparticles were obtained.

The average particle size of the above particles was measured with a "Nanotrac" light scattering photometer (NIKKISO Co., Ltd.) and found to be 23 nm.

Example 8

Milk-derived casein (100 mg; Wako Pure Chemical Industries, Ltd.) was mixed with 50 mM phosphate buffer (pH 10, 10 mL). Palmitoylascorbic acid (1 mg; Wako Pure Chemical Industries, Ltd.) was dissolved in ethanol (0.2 mL). The two different solutions were mixed together. Hydrochloric acid was added thereto so that the pH was adjusted to 7. Thus, casein nanoparticles were obtained.

The average particle size of the above particles was measured with a "Nanotrac" light scattering photometer (NIKKISO Co., Ltd.) and found to be 30 mu.

Example 9

Acid-treated gelatin (10 mg) and TG-S (5 mg; Ajinomoto Co., Inc.) were dissolved in water (1 mL). The gelatin solution (1 ml) was injected into ethanol (10 mL) in which tocopherol (1.7 mg) had been dissolved with the use of a microsyringe at an external temperature of 40° C. during stirring at 800 rpm. Thus, gelatin nanoparticles were obtained. The gelatin nanoparticles were allowed to stand at an external temperature of 55° C. for 5 hours for enzymatic crosslinking.

The average particle size of the above particles was measured with a "Microtrac" light scattering photometer (NIKKISO Co., Ltd.) and found to be 95 nm.

Example 10

Milk-derived casein (100 mg; Wako Pure Chemical Industries, Ltd.) was mixed with 50 mM phosphate buffer (pH 10, 10 mL). Pantothenyl ethyl ether (400 mg; Wako Pure Chemical Industries, Ltd.) was dissolved in ethanol (0.8 mL). The two different solutions were mixed together. Hydrochloric acid was added thereto so that the pH was adjusted to 6. Thus, casein nanoparticles were obtained.

The average particle size of the above particles was measured with a "Nano-ZS" light scattering photometer (Malvern Instruments Ltd) and found to be 24 nm.

Test Example 1

The dispersions of nanoparticles containing active substances for hair described in Examples 2 to 6 were preserved at room temperature for 1 month. Thereafter, average particle size measurement was carried out using a Microtrac (NIKKISO Co., Ltd.).

As Comparative example 1, a "NanoImpact" synthetic polymer (PLGA) nanoparticle dispersion (Hosokawa Micron Corporation) was used.

Table 1 shows measurement results obtained in Test example 1.

TABLE 1

| Test example 1 | | | | | | |
|---|---|---|---|---|---|---|
| | Comparative example 1 | Example 2 | Example 3 | Example 4 | Example 5 | Example 6 |
| When prepared | 600 nm | 83 nm | 57 nm | 124 nm | 55 nm | 201 nm |
| 1 month later | N.D. | 90 nm | 63 nm | 141 nm | 62 nm | 220 nm |

N.D.: Not detected

Test Example 2

Hairless Rat Excised Skin Test

A 2-cm square piece of nonwoven cloth absorbing 400 µl of the casein nanoparticle dispersion prepared in Example 1 was applied to hairless rat excised skin and the skin was allowed to stand for 30 minutes. Then, the skin was embedded within an OCT compound (Sakura Finetek Co., Ltd.) and frozen with liquid nitrogen. A frozen section was prepared from the skin with the use of a cryostat (Carl Zeiss). The section was immobilized and enclosed on a prepared slide with the use of a DAPI-containing mounting agent, followed by fluorescence microscopic observation.

Comparative Example 2

No Application

Comparative Example 3

With the use of the following dispersion, fluorescence microscopic observation was conducted as with Test example 2.

Milk-derived casein (100 mg; Wako Pure Chemical Industries, Ltd.) was mixed with distilled water (10 mL). Coumarin 6 (0.015 mg; Wako Pure Chemical Industries, Ltd.) was dissolved in ethanol (0.1 mL). A dispersion was obtained by mixing the two different solutions.

Comparative Example 4

With the use of the following solution, fluorescence microscopic observation was conducted as with Test example 2.

A solution was obtained by dissolving coumarin 6 at a concentration of 0.15 mg/mL in a 50% ethanol aqueous solution.

Test Example 3

SD Rat In Vivo Test

A SD rat was subjected to anesthetic injection. Thereafter, a 2-cm square piece of nonwoven cloth absorbing 400 µl of the casein nanoparticle dispersion prepared in Example 1 was applied to the abdominal skin of the rat and the skin was allowed to stand for 60 minutes. The skin was embedded within an OCT compound (Sakura Finetek Co., Ltd.) and frozen with liquid nitrogen. A frozen section was prepared from the skin with the use of a cryostat (Carl Zeiss). Then, the section was immobilized and enclosed on a prepared slide with the use of a DAPI-containing mounting agent, followed by fluorescence microscopic observation.

Comparative Example 5

With the use of the following solution, fluorescence microscopic observation was conducted as with Test example 3.

A solution was obtained by dissolving coumarin 6 at a concentration of 0.15 mg/mL in a 50% ethanol aqueous solution.

FIGS. 1*a* to 6*a* show fluorescence photomicrographs of the hairless rat excised skins and the SD rat skin sections in Comparative examples 2, 3, 4, and 5 and Test examples 2 and 3. FIGS. 1*b* to 6*b* show DAPI-stained tissue images corresponding to the visual fields in FIGS. 1*a* to 6*a*.

Test Example 4

Dorsal hair of C3H mice at the trichogenous or dormant phase were cut with a hair clipper. On the next day, the mice were shaved with a shaver. The water dispersions of protein nanoparticles containing hair growth agents prepared in Examples 2 to 5 were separately applied to all shaved areas once daily. The degree of ability to cause phase transition to the growth phase in mouse dorsal hair follicles was examined. As a result, hair growth was promoted and activity of causing hair cycle transition from the dormant phase to the growth phase was observed.

Test Example 5

Figure 7:
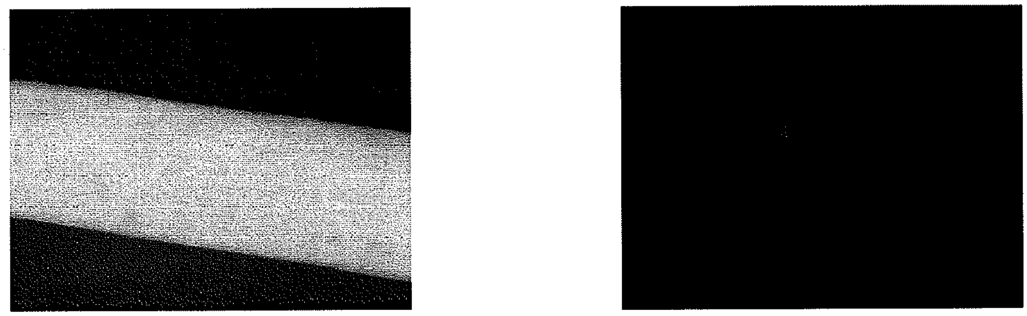
FIG. 7 shows the results of fluorescence microscopic observation in Test example 5.
Figure 8:
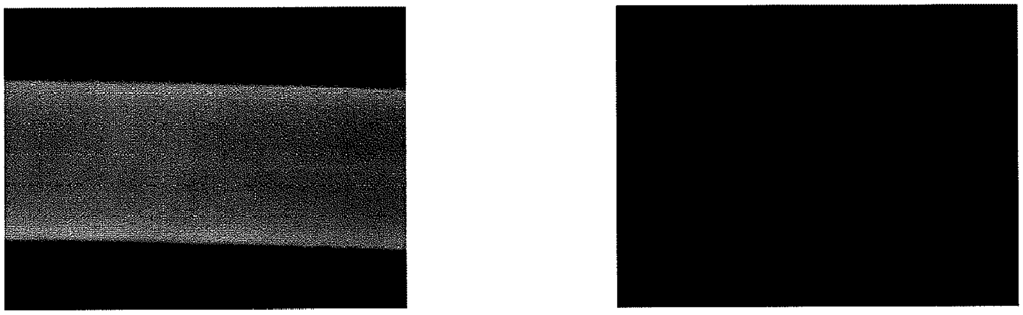
FIG. 8 shows the results of fluorescence microscopic observation in Test example 5.

Coumarin 6 at a concentration of 0.15 mg/mL was dissolved in the dispersion prepared in Example 1 and in a 50% ethanol aqueous solution. The obtained solutions at 25° C. were separately applied to goat hair. After 30 minutes of reaction time, goat hair was washed and dried. The color tone of the obtained dyed hair was observed. In the case of Example 1, good permeation was confirmed. FIG. 7*a* shows a fluorescence photomicrograph of a goat hair surface (Example 1). FIG. 7*b* shows fluorescence photomicrograph of a goat hair cross section. FIG. 8*a* shows a fluorescence photomicrograph of a goat hair surface (ethanol solution). FIG. 8*b* shows fluorescence photomicrograph of a goat hair cross section.

Test Example 6

Sensory Evaluation

A human hair bundle 15 cm in length, 1 cm in width, and 1 g in weight was immersed in the composition (5 mL) obtained in Example 10 for approximately 30 seconds and sufficiently dried. The hair bundle was designated as a test hair bundle. And an untreated hair bundle was designated as a reference hair bundle. The hair bundles were subjected to five-grade sensory evaluation in terms of smoothness, elasticity, volume/strength, and uniformity in accordance with the criteria listed in Table 2. Evaluation was carried out by 5 persons. The mean values are listed in Table 3.

TABLE 2

| Evaluation criteria | |
|---|---|
| (Smoothness) | (Elasticity) |
| 4: Sufficient smoothness | 4: Test hair: Superior in elasticity |
| 3: Normal smoothness | 3: Test hair: Slightly superior in elasticity |
| 2: No obvious difference | 2: No obvious difference |

TABLE 2-continued

| Evaluation criteria | |
|---|---|
| 1: Poor smoothness<br>0: No smoothness | 1: Reference hair: Slightly superior in elasticity<br>0: Reference hair: Superior in elasticity |
| (Volume/Strength) | (Uniformity) |
| 4: Test hair: Superior in volume and strength<br>3: Test hair: Slightly superior in volume and strength<br>2: No obvious difference<br>1: Reference hair: Slightly superior in volume and strength<br>0: Reference hair: Superior in volume and strength | 4: Test hair: Superior in uniformity<br>3: Test hair: Slightly superior in uniformity<br>2: No obvious difference<br>1: Reference hair: Slightly superior in uniformity<br>0: Reference hair: Superior in uniformity |

TABLE 3

| | Sensory evaluation | | | |
|---|---|---|---|---|
| | Smoothness | Elasticity | Volume/Strength | Uniformity |
| Test hair | 3.8 | 3.4 | 3.8 | 3.6 |
| Reference hair | 1.0 | 2.0 | 1.8 | 2.0 |

What is claimed is:

1. A cosmetic which comprises casein nanoparticles having an average particle size of 10 nm to 83 nm and containing an effective amount of a hair growth agent selected from the group consisting of at least one of glycyrrhetic acid or derivatives thereof and pantothenyl ethyl ether.

2. The cosmetic according to claim 1, wherein the cosmetic is selected from rinses, conditioners, hair packs, hair tonics, or hair sprays.

* * * * *